(12) United States Patent
Ganesan et al.

(10) Patent No.: US 10,393,705 B2
(45) Date of Patent: Aug. 27, 2019

(54) METHOD AND SYSTEM FOR DETERMINATION OF GEOMETRIC FEATURES IN OBJECTS

(71) Applicant: General Electric Company, Schenectady, NY (US)

(72) Inventors: Baskaran Ganesan, Acton, MA (US); Satheesh Jeyaraman, Karnataka (IN); Albrecht Maurer, Alzenau (DE)

(73) Assignee: General Electric Company, Schenectady, NY (US)

( * ) Notice: Subject to any disclaimer, the term of this patent is extended or adjusted under 35 U.S.C. 154(b) by 23 days.

(21) Appl. No.: 14/415,583

(22) PCT Filed: Jul. 18, 2013

(86) PCT No.: PCT/US2013/050997
§ 371 (c)(1),
(2) Date: Jan. 17, 2015

(87) PCT Pub. No.: WO2014/022104
PCT Pub. Date: Feb. 6, 2014

(65) Prior Publication Data
US 2015/0212048 A1      Jul. 30, 2015

(30) Foreign Application Priority Data
Jul. 31, 2012   (IN) ............................ 3133/CHE/2012

(51) Int. Cl.
*G01N 29/06*       (2006.01)
*G01N 29/07*       (2006.01)
(Continued)

(52) U.S. Cl.
CPC ............. *G01N 29/04* (2013.01); *G01B 17/00* (2013.01); *G01D 5/12* (2013.01); *G01N 29/043* (2013.01);
(Continued)

(58) Field of Classification Search
CPC ........ G01N 29/04; G01N 29/07; G01N 29/11; G01N 29/4418; G01N 29/043;
(Continued)

(56) References Cited

U.S. PATENT DOCUMENTS 5,285,689 A * 2/1994 Hapstack ............. G01N 29/265
324/220
2003/0101007 A1* 5/2003 Dubois .............. G01N 29/0645
702/39

(Continued)

FOREIGN PATENT DOCUMENTS

CN       101135673 A      3/2008
CN       102007402 A      4/2011
(Continued)

OTHER PUBLICATIONS

International Search Report issued in connection with corresponding application PCT/US13/050997 dated Nov. 6, 2013.
(Continued)

*Primary Examiner* — Natalie Huls
*Assistant Examiner* — Suman K Nath
(74) *Attorney, Agent, or Firm* — Mintz Levin Cohn Ferris Glovsky and Popeo, P.C.

(57) ABSTRACT

A method and system for determination of geometric features in an object is provided. The method includes receiving at least one geometric feature response to an ultrasound beam incident on the object. The incident ultrasound beam is produced from one of a plurality of ultrasound transducers. Further, a volumetric representation of the object is generated based on a plurality of object parameters. The volumetric representation of the object and a plurality of transducer parameters are used to generate a predicted beam traversal path in the object. The predicted beam traversal path is utilized to generate a temporal map of predicted time (Continued)

of flight geometric feature response to the ultrasound beam. A position on the volumetric representation of the object is determined as the location of the geometric feature, when the received geometric feature response is equivalent to the predicted time of flight geometric feature response corresponding to the position.

17 Claims, 4 Drawing Sheets

(51) Int. Cl.
    *G01N 29/44* (2006.01)
    *G01N 29/04* (2006.01)
    *G01B 17/00* (2006.01)
    *G01D 5/12* (2006.01)

(52) U.S. Cl.
    CPC .......... *G01N 29/069* (2013.01); *G01N 29/07* (2013.01); *G01N 29/4418* (2013.01)

(58) Field of Classification Search
    CPC ....... G01N 2291/267; G01N 2291/011; G01N 2291/015; G01N 2291/2672; G01N 2291/2675; G01N 2291/2677
    USPC .......... 73/600, 602, 598, 622, 597, 648, 599
    See application file for complete search history.

(56) References Cited

U.S. PATENT DOCUMENTS

| | | |
|---|---|---|
| 2005/0139006 A1 | 6/2005 | Lorraine et al. |
| 2008/0053232 A1 | 3/2008 | Hegen et al. |
| 2009/0032329 A1 | 2/2009 | Ihn |
| 2010/0131246 A1 | 5/2010 | Volker et al. |
| 2010/0249570 A1* | 9/2010 | Carson ................. A61B 5/0059 600/407 |
| 2010/0299095 A1* | 11/2010 | Ihn ....................... G01N 29/223 702/113 |
| 2013/0263667 A1* | 10/2013 | Volker ................... G01B 17/02 73/598 |

FOREIGN PATENT DOCUMENTS

| | | |
|---|---|---|
| EP | 2439527 A1 | 4/2012 |
| JP | S60128375 A | 7/1985 |
| JP | 2002257802 A | 9/2002 |
| JP | 2004117137 A | 4/2004 |
| JP | 2005148009 A | 6/2005 |
| JP | 2005195594 A | 7/2005 |
| JP | 2006-284578 A | 10/2006 |
| JP | 2010071983 A | 4/2010 |
| JP | 2010519509 A | 6/2010 |

OTHER PUBLICATIONS

Unofficial English translation of Japanese Office Action issued in connection with corresponding JP Application No. 2015-525443 dated Mar. 14, 2017.

Unofficial English translation of Japanese Search Report issued in connection with corresponding JP Application No. 2015-525443 dated Apr. 20, 2017.

Unofficial English translation of Chinese Office Action issued in connection with corresponding CN Application No. 201380040689.4 dated May 24, 2016.

Decision of Refusal issued in connection with corresponding JP Application No. 2015-525443 dated Jan. 30, 2018.

* cited by examiner

METHOD AND SYSTEM FOR DETERMINATION OF GEOMETRIC FEATURES IN OBJECTS

BACKGROUND

Embodiments of the present invention relate generally to the field of ultrasound inspection systems, and specifically, to a method and system for determination of geometric features in objects.

Use of ultrasound beams in the field of non-destructive testing (NDT) for objects is well known and widely used. Objects such as pipes, solid rods, metal sheets, and metal billets are often inspected through the use of ultrasound beams. Ultrasound inspections are used to determine the presence of geometric features such as welds, porosity, corrosion, slag, cracks, and welding defects in the objects.

In ultrasound inspection the object is exposed to ultrasound beams from transducers placed across the length of the object. Responses to the incident ultrasound beams from different parts in the object are collected by the transducers. The amplitudes of the responses are then analyzed to locate geometric features in the object.

In practical applications, an object is passed through an array of transducers arranged in a particular order to transmit ultrasonic beams into the object with various angles of incidence. Every region of interest within the object to be inspected is passed through this configuration of transducers to generate responses to the ultrasound beams transmitted from each transducer. Hence, interrogation of each object yields a large amount of data during testing. The large amount of data thus received is utilized to generate response charts that plot the amplitudes of the responses against positions of the geometric features in the object with respect to a reference point on the object. The reference point is typically fixed by an operator of the inspection system. Thus, to accurately locate a geometric object, the operator has to manually sift through multiple response charts that display output obtained from the geometric features as a result of the ultrasound beams from different transducers in the configuration.

In typical ultrasound inspection systems designed to inspect hollow pipes, for example, 34 ultrasound transducers are arranged to inspect the pipe. Each transducer scans the pipe and generates geometric feature responses at fixed points along the circumference of the pipe. Response data generated for one transducer for one pipe, thus, requires several kilobytes of memory storage space. Response data from the inspection system for the entire pipe, therefore, amounts to requiring megabytes of memory space.

To handle such voluminous data generated for every inspected object by these inspection systems, installation of a data management system is required. Data management systems that handle data loads of a typical inspection setup handling hundreds of test objects everyday tend to be expensive owing to the amount of data being generated and processed. To avoid expenses related to these data management systems, ultrasound inspection systems store only a part of the data obtained from the transducers by selecting specific positions in the object to generate response charts. For example, in certain systems maximum amplitudes observed at locations between fixed distances in the object are used to generate the response chart. These data reduction techniques add errors to localization of geometric features in objects since the location of the geometric feature is now determined as a function of the fixed distance as opposed to an exact location.

Moreover, the operator spends a lot of time analyzing the data obtained from inspection systems to localize the geometric feature in the object. Errors are introduced in the localization of geometric features as a result of manual interpretation of the response charts. Further, operator costs are also multiplied and added to the cost of utilization of the current-day inspection systems.

Hence, there is a need for a method and system to analyze the limited data obtained from inspection systems and presenting the geometric feature output in a form that reduces operator efforts in localization of the geometric features.

BRIEF DESCRIPTION

In one embodiment, a method for determining location of at least one geometric feature in an object is provided. The method includes receiving at least one geometric feature response to an ultrasound beam incident on the object. The ultrasound beam incident on the object is generated from one of a plurality of ultrasound transducers placed along the object. The method further includes generating a volumetric representation of the object based on a plurality of object parameters. Further, the method includes generating a temporal map of a predicted time of flight geometric feature response to the ultrasound beam based on a predicted ultrasound beam traversal path in the object and originating from the ultrasound transducer. The predicted ultrasound beam traversal path is generated based on the volumetric representation of the object, and a plurality of transducer parameters. Furthermore, the method includes the step of determining a position on the volumetric representation of the object as the location of the geometric feature, when the received geometric feature response is equivalent to the predicted time of flight geometric feature response corresponding to the position.

In another embodiment, a system for determination location of at least one geometric feature in an object is provided. The system includes at least one ultrasound transducer configured to transmit an ultrasound beam on the object and receive at least one geometric feature response to the ultrasound beam. The system further includes a processor. The processor is configured to generate a volumetric representation of the object based on a plurality of object parameters. Further, the processor is also configured to generate a temporal map of predicted a time of flight geometric feature response to the ultrasound beam based on a predicted ultrasound beam traversal path in the object and originating from the ultrasound transducer. The predicted ultrasound beam traversal path is generated based on the volumetric representation of the object, and a plurality of transducer parameters. Furthermore, the processor is configured to determine a position on the volumetric representation of the object as the location of the geometric feature, when the received geometric feature response is equivalent to the predicted time of flight geometric feature response corresponding to the position.

In yet another embodiment, a non-transitory computer readable media that causes a processor to execute a method of determining location of at least one geometric feature response on an object is provided. The non-transitory computer readable media includes program instructions to receive geometric feature response to an ultrasound beam incident on the object. The ultrasound beam incident on the object is produced by at least one ultrasound transducer. Further, the computer readable media includes program instructions to generate a volumetric representation of the object based on a plurality of object parameters. Furthermore, the computer readable media includes program instructions to generate a temporal map of predicted a time of flight geometric feature response to the ultrasound beam based on a predicted ultrasound beam traversal path in the object and originating from the ultrasound transducer. The predicted ultrasound beam traversal path is generated based on the volumetric representation of the object, and a plurality of transducer parameters. The computer readable media also includes program instructions to determine a position on the volumetric representation of the object as the location of the geometric feature, when the received geometric feature response is equivalent to the predicted time of flight geometric feature response corresponding to the position.

DRAWINGS

The present invention will be better understood from reading the following description of non-limiting embodiments, with reference to the attached drawings, wherein below.

DETAILED DESCRIPTION

Reference will be made herein to exemplary embodiments of the invention, examples of which are illustrated in the accompanying drawings. Wherever possible, the same reference numerals used throughout the drawings refer to the same or like parts.

Embodiments of the invention described herein relate to a method and a system for the determination of geometric features in an object. Ultrasound beams, which are produced using at least one ultrasound transducer, are transmitted so as to be incident on the object being inspected. The ultrasound transducers are arranged to cover the entire geometry of the area of the object to be inspected. One or more geometric features in the object cause a change in the ultrasound beam in the object and this change in the ultrasound beam is termed a geometric feature response. Examples of changes in the ultrasound beam include, but are not limited to, reflection, scattering, refraction, and deviation in the path of the beam. These responses are received by the ultrasound transducers and are processed to obtain amplitude and time of flight information. The amplitude and time of flight information of the geometric feature responses are processed to determine the location of the one or more geometric features in the object.

To obtain the location of at least one of the one or more geometric features from the received geometric feature responses, a volumetric representation of the object is generated. The volumetric representation of the object is generated using a plurality of object parameters such as the length of the object, diameter of the object, and thickness of the object. Further, a temporal map of a predicted time of flight geometric feature responses is generated. The temporal map is generated based on a predicted ultrasound beam traversal path. The predicted ultrasound beam traversal path is generated based on a plurality of transducer parameters and the volumetric representation of the object. The transducer parameters utilized to generate the beam traversal path include, but are not limited to, angle of incidence of the transducer, size of the transducer, geometry of the transducer, and the position of the transducer with respect to the object. The received geometric responses are then compared with the temporal map to determine the location of the geometric feature on the volumetric representation. The foregoing is described in greater detail in the subsequent paragraphs with the help of accompanied drawings.

Figure 1:
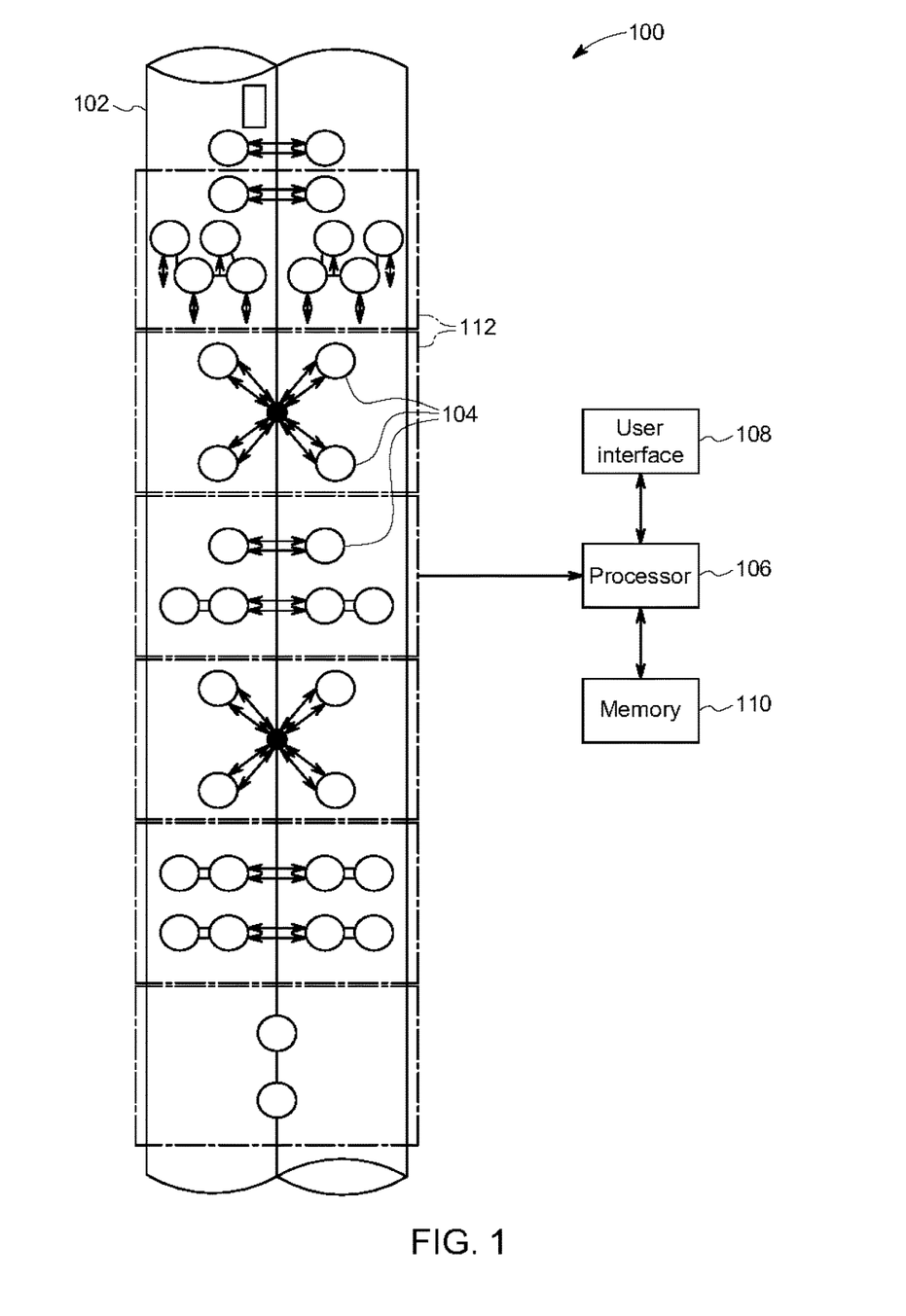
FIG. 1 illustrates an exemplary embodiment of an ultrasound inspection system for determining locations of geometric features in an object.

FIG. 1 illustrates an exemplary embodiment of an ultrasound inspection system 100. The ultrasound inspection system 100 includes an object 102 being tested, a plurality of ultrasound transducers 104, a processor 106, a user interface 108, and a memory 110. The ultrasound inspection system 100 non-destructively tests the object 102 to find the presence and location of geometric features in the object. The object being tested 102, according to certain embodiments, can be a hollow structure or a solid structure. In particular, examples of object 102 include, but are not limited to, pipes, sheets, rods, nozzles, and billets. The geometric features being inspected through the ultrasound inspection system 100 may include, but are not limited to, anomalies in the object 102, cracks, welds, defects in welds, porosity, corrosion, and slag, for example. Different configurations, based on the arrangement of the plurality of ultrasound transducers 104 with respect to the object 102, are possible to ensure that the relevant object geometry is covered. Different types of transducer configurations include, but are not limited to longitudinal, transverse, heat affected zone (HAZ) and tandem configuration of transducers. The ultrasound transducer 104 configuration shown in FIG. 1 is decided based on the type of geometric feature to be located. The angles at which the transducers 104 are arranged with respect to the object 102 provide for different incident angles to the ultrasound beams transmitted by the transducers 104. The plurality of ultrasound transducers 104 can be unidirectional transducers or bi-directional transducers. In one embodiment, the transducers 104 may represent Electromagnetic Acoustic Transducers (EMATs) used to generate ultrasound beams that are incident on the object 104.

The processor 106, in certain embodiments, may comprise a central processing unit (CPU) such as a microprocessor, or may comprise any suitable number of application specific integrated circuits working in cooperation to accomplish the functions of a CPU. The processor 106 may include a memory 110. The memory 110 can be an electronic, a magnetic, an optical, an electromagnetic, or an infrared system, apparatus, or device. Common forms of memory 110 include hard disks, magnetic tape, Random Access Memory (RAM), a Programmable Read Only Memory (PROM), and EEPROM, or an optical storage device such as a re-writeable CDROM or DVD, for example. The processor 106 is capable of executing program instructions, related to the system for determining geometric features in the object 102, and functioning in response to those instructions or other activities that may occur in the course of determining geometric features. Such program instructions will comprise a listing of executable instructions for implementing logical functions. The listing can be embodied in any computer-readable medium for use by or in connection with a computer-based system that can retrieve, process, and execute the instructions. Alternatively, some or all of the processing may be performed remotely by additional processors 106.

The ultrasound transducers 104 may be placed on a stationary electronic arm or a movable electronic arm, for example. In one embodiment, the processor 106 may be configured to move such an electronic arm (not shown) holding the transducers 104 along the length of the object 102 to cover the geometry to be inspected. Alternatively, the electronic arm may be held stationary while the object 102 is moved across the array of ultrasound transducers 104. Further still, both the electronic arm and the object 102 may be moved in coordination such that ultrasound beams from the transducers 104 can be transmitted so as to be incident on the area of the object 102 to be inspected. In certain embodiments, the object 102 may be placed on a movable rail to move and/or rotate the object 102. In certain other embodiments, the ultrasound transducers 104 may be placed in a handheld probe assembly that may be moved along the length of the object 102 for inspection by an operator.

During inspection each of the ultrasound transducers 104 generate and transmit ultrasound beams to be incident on the object 102. The ultrasound beams travel from the ultrasound transducers 104 into the object 102 and geometric feature responses, caused due to the presence of geometric features in the object 102, are received by the transducers 104. The ultrasound transducers 104, when bidirectional, are configured to receive the responses from the geometric features in the object 102. In other configurations, when transducers 104 are unidirectional, one transducer 104 transmits the ultrasound beam, and another transducer 104 is arranged so as to collect the responses from the geometric features in the object 102. For example, in tandem configuration of transducers 104, two transducers 104 are placed on one side of the area of interest of the object 102 to transmit ultrasound beams, and one transducer 104 is placed to receive the responses from the geometric features.

The processor 106 receives the geometric feature responses from the transducers 104 to generate a response chart that captures geometric feature response amplitudes from different parts of the object 102. In one embodiment, the processor 106 is configured to display the response chart on a display screen. In another embodiment, the processor 106 is configured to display the response on the user interface 108.

The response chart generated by the processor 106 is then analyzed by the operator to determine the presence and location of geometric features in the object 102. During analysis, an amplitude threshold is defined for the geometric feature response. The operator identifies those positions corresponding with amplitudes greater than the defined threshold as being positions corresponding to the geometric features. An exemplary response chart for the ultrasound inspection system 100 is provided in FIG. 2.

Before the object 102 is tested, a reference run of the inspection may be carried out by the ultrasound imaging system 100. In the reference run, ultrasound beams generated from the ultrasound transducers 104 are transmitted to be incident on a reference object with known locations of geometric features. Amplitudes of responses received by the transducers 104 from the reference object are then used to determine if the responses from the known locations of geometric features are above the defined threshold. Calibration operations, such as changing the position of one or more of the ultrasound transducers 104, may be carried out to ensure that the position determined from the amplitude matches the known location.

Figure 2:
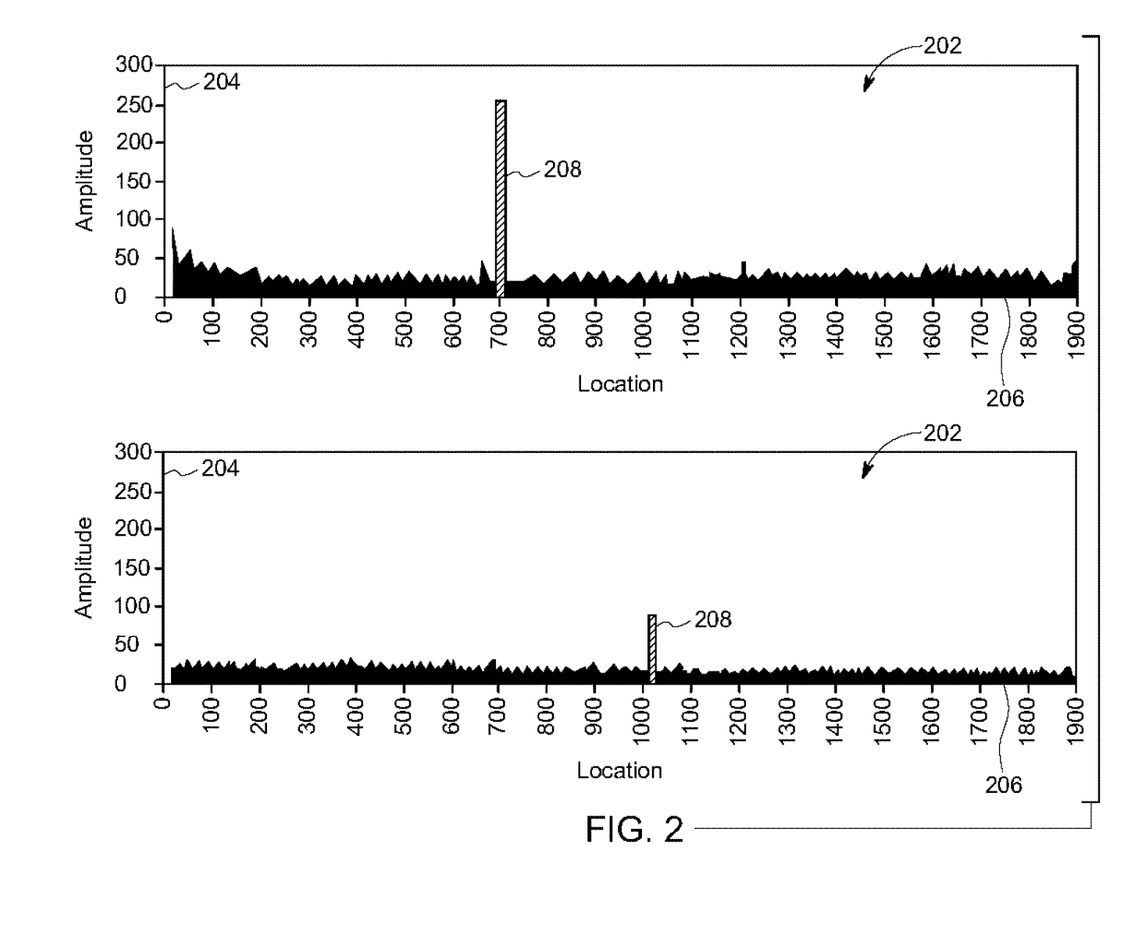
FIG. 2 illustrates an exemplary geometric feature response chart obtained from the ultrasound inspection system of FIG. 1.

FIG. 2 is an exemplary geometric feature response charts 202 generated by the processor 106 of the ultrasound inspection system 100 from the object 102 and displayed on the user interface 108. The response chart 202 in FIG. 2 is a 1-dimensional response chart representing the responses received from the object 102 to the incident ultrasound beam. In certain embodiments, the geometric feature responses that are received by the transducers 104 are stored in the memory 110. The processor 106 reads this data stored in the memory 110 to generate the response charts 202. In certain embodiments, the transducers 104 are configured to transmit the geometric feature responses to the processor 106 through a communication channel between the transducers 104 and the processor 106. The communication channel may be a wired/wireless network. In other embodiments, the geometric feature response is transmitted to the processor 106 through a communication channel between the inspection system 100 and the processor 106. In certain embodiments, the processor 106 may be a part of a remote server system that is in communication with the ultrasound inspection system 100. The ultrasound transducers 104 may then be coupled to at least one transmitter that is configured to transmit geometric feature responses to the processor 106. In the response chart of FIG. 2, amplitudes 204 of responses to the incident ultrasound beams from geometric features in the object 102 are plotted against locations 206 of the response in the object 102. The amplitudes may represent units of frequency, while the locations 206 of the responses are measured with respect to a reference point on the object 102 and may represent units of length, for example. To determine the presence of a particular geometric feature in the object, an amplitude threshold is defined by the operator. Positions for which the amplitude values lie above the threshold correspond to locations of the geometric features. For example, if the amplitude of the response corresponding to the point 208 crosses the defined threshold, it may be concluded that a geometric feature is present at a point on the location axis 206 that corresponds to the point 208. While inspection is being carried out by the ultrasound inspection system 100 on the object 102, such response charts are generated by the processor 106 for each ultrasound transducer from the transducers 104. The response charts may be observed by the operator either on a paper or via a display.

In certain embodiments, the geometry of the object 102 is divided in smaller segments, termed the 'pitch' of the object 102. For example, for the object 102 illustrated in FIG. 1, the length of the object 102 may be split in smaller segments 112, where each segment is termed the pitch in the object 102. In certain embodiments, the object 102 may be divided in segments 112 of different sizes. The object 102 may also have segments 112 of the same size. In certain embodiments, in the response chart, a maximum value from the amplitudes of responses for every pitch of the object 102 is plotted. Further, in certain embodiments, for each pitch of the object 102, time of flight information is collected for the location corresponding to the maximum amplitude geometric feature response.

In the present technique, the time of flight information for the responses received by the transducers 104 from different points in the object 102 is used to determine the presence of geometric features in the object 102. In one embodiment, each of the received geometric feature responses is compared with points in a temporal map of a predicted time of flight geometric feature response. The temporal map of the predicted time of flight geometric feature response is generated by the processor 106 based on a predicted beam traversal path. The processor 106 generates the predicted beam traversal path based on a plurality of transducer parameters and a volumetric representation of the object 102. The volumetric representation of the object 102 is generated by the processor 106 based on a plurality of object parameters. The object parameters include, but are not limited to, object thickness, object diameter, object geometry and object length. Object geometry includes, but is not limited to, details pertaining to shape of the object 102, angles of curvatures, cone angles, and bends observed in the object 102. Based on the available geometric information of the object 102, the object 102 is reconstructed by the processor 106 to generate a 3-dimensional image of the object 102. The 3-dimensional image, in certain embodiments, is generated by the processor 106 by utilizing 3-dimensional modeling software such as AutoCAD™ and CATIA™. In certain embodiments, a geometrically proportional physical model of the object 102 is utilized as the volumetric representation of the object 102.

Figure 3:
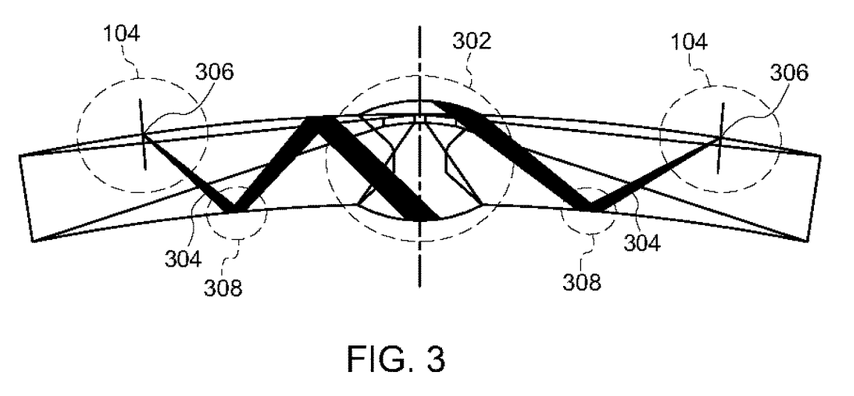
FIG. 3 illustrates an exemplary predicted beam traversal path according to one embodiment of the present invention.

FIG. 3 illustrates exemplary predicted beam traversal paths 304 of the ultrasound beams transmitted by the transducers 104 in the object 102. The predicted beam traversal paths 304 are a representation of a path that the ultrasound beams transmitted by the ultrasound transducers 104 take in the object 102. The predicted beam traversal paths 304 are determined based on the volumetric representation of the object 102, and a plurality of transducer parameters specific to the transducers 104. The predicted beam traversal paths 304 are generated based on the angle of incidence of the ultrasound transducers 104 from which the ultrasound beams are transmitted. The angle of incidence of the transducers 104 is selected based on the area of interest 302 of the object 102 that needs to be inspected. The angle of incidence for the transducers 104 is selected such that ultrasound beam is incident on the entire desired area of interest 302. Further, the location of the transmitting ultrasound transducers 104 along the object 102, and operating frequency of the transmitting transducers 104 also influence the beam traversal paths 304 in the object 102. In other embodiments, a skew angle (i.e. whether the transducers 104 are "in plane" or "out of plane" with respect to the object 102) associated with the transducers 104 may also be utilized to generate the predicted beam traversal paths 304. In certain embodiments, an operator of the system 100 provides the plurality of transducer parameters to the processor 106 through the user interface 108. In the exemplary illustration, item 306 represents the points of origin of the beams 304 from the transducers 104. The beams originate from the points 306 in the ultrasound transducers 104 and undergo redirections within the object 102. The beams continue to travel in the object 102 and, in certain embodiments, may undergo multiple redirections in path. Item 308 is an exemplary point of redirection for the beams 304 in the object 102.

The determination of the beam traversal paths 304 involves determination of the beam traversal path length along with the points of redirection. The path length and the points of redirection are determined based on the angle of incidence of the transmitting ultrasound transducers 104 and physical principles that govern beam propagation in the object 102. Principles such as Ultrasound Ray Theory, Snell's Law of refraction, laws of acoustic reflection, and Fermat's principle that determine how beams travel through solid and gaseous bodies are utilized to determine the predicted beam traversal paths 304.

Unfocused ultrasound beams are transmitted with a cone angle that governs a lateral spread of the beam, termed beam spread, along the beam traversal path. The ultrasound beam spread for the beam emanating from the transducers 104 is determined based on the size of the transducers 104, geometry of the transducers 104, and the angle of incidence of the transducers 104. The determined beam spread for the beam emanating from the transducers 104 is applied across the beam traversal path length to generate the predicted beam traversal paths 304.

In certain embodiments, it is assumed that the speed of sound in the object 102 is constant. The speed of sound can also be calculated at different locations in the object 102. The speed of sound at different locations influences the predicted beam traversal paths 304. In certain embodiments, the speed of sound at different locations is utilized to correct the predicted beam traversal paths 304. According to certain embodiments, the speed of sound in the object 102 may be calculated by utilizing transducers 104 located at two points along the object 102. One of the transducers 104 transmits the ultrasound beam, and another transducer 104 receives the transmitted ultrasound beam. Based on the known distance between the transducers 104, and the time taken by the by ultrasound beam to travel from one transducer 104 to the other transducer 104, the speed of sound is calculated.

Utilizing the predicted beam traversal paths 304, the temporal map of the predicted time of flight geometric feature response for each of the incident ultrasound beams is determined. During generation of the temporal map of predicted time of flight geometric feature response for each of the beams, the respective predicted beam traversal path 304 is divided into smaller rays. Over each ray path, presence of geometric features is assumed. The predicted beam traversal path 304 is also utilized to determine a path of the response back to the transducers 104. The speed of the ultrasound beam in the object 102 and distance covered by the ultrasound beam from the origin 306 of the beam on the beam traversal path 304 to the assumed geometric feature and the beam's return to the transducers 104 are utilized to calculate the time of flight for the ultrasound beam from each geometric feature in the ray path. The temporal map of the predicted time of flight geometric feature response may be a list of time of flight information for each of the ultrasound beams calculated based on the assumption of the presence of geometric features along every ray in each predicted beam traversal path 304.

According to certain embodiments, the reference run of inspection is utilized to calculate the speed of the ultrasound beam in the object 102. In the test run, when the location of the geometric feature is known, ultrasound beams from one transducer 104 are transmitted so as to be incident on the geometric feature. The time of flight of the geometric feature response thus collected is used to calculate the speed of the ultrasound beam. Geometric feature responses collected for ultrasound beams transmitted by multiple transducers 104 may also be used to calculate the speed of ultrasound beams in the object 102.

The temporal map of the predicted time of flight geometric feature response is then compared with the received geometric feature response. The received geometric feature response includes time of flight information for the locations within the object 102 where the amplitude of the geometric feature response is greater than the defined threshold. The location corresponding to a point from the temporal map of the predicted time of flight geometric feature response that is equivalent to the time of flight of the received geometric feature response is determined as the location of the geometric feature.

In certain embodiments, the temporal map of the predicted time of flight geometric feature response is generated based on the predicted beam traversal path 304 for ultrasound beams originating from more than one transducer 104 that are arranged at an angle with respect to the object 102 to be able to transmit ultrasound beams that can be incident on the area of interest of the object 102. For example, in FIG. 3, the two transducers 104 are arranged on the object 102 to transmit ultrasound beams into the same area of interest 302 of the object 102. Hence, two predicted beam traversal paths 304 from two transducers 104 are determined. The location of a geometric feature in the area of interest 304 is determined individually based on each of the predicted beam traversal paths 304. The locations determined through two different predicted beam traversal paths 302 are compared to determine the final location of the geometric feature.

According to certain embodiments, when multiple transducers 104 are arranged to transmit ultrasound beams so as to be incident on the area of interest 302, the amplitude information of the geometric feature responses received by the transducers 104 may be utilized to determine the size of the geometric feature. For example, for a particular geometric feature response it may be determined from the predicted beam traversal path 304 whether the ultrasound beam was incident on the geometric feature or whether the geometric feature was present at one of the edges of the ultrasound beam. Hence, the amplitude of the geometric feature response for such an ultrasound beam may not give an accurate estimate of the size of the geometric feature. The predicted beam traversal path 304 for other transducers 104 may be utilized to determine the ultrasound beam that is incident on the particular geometric feature and the size of the geometric feature may be determined based on the amplitude information included in the geometric feature response for the other transducer 104.

Figure 4:
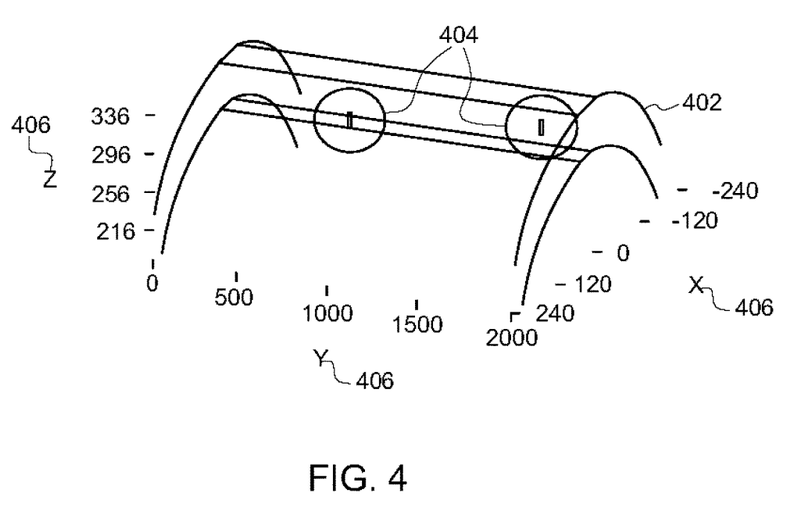
FIG. 4 illustrates an exemplary representation of location of geometric features on a volumetric representation of an object according to one embodiment of the present invention.

FIG. 4 illustrates an exemplary representation of the location of geometric features on a volumetric representation of an object according to one embodiment of the present invention. Item 404 depicts locations of one or more geometric features in the volumetric representation 402 of the object 102. The volumetric representation 402 of the object 102 is generated based on object parameters like object size, object diameter, and object thickness. The object parameters are provided to the processor 106, in certain embodiments, by the operator through the user interface 108 to generate the volumetric representation 402. The volumetric representation 402 is further used, along with physical principles that govern beam propagation, to determine the predicted beam traversal path 304. The predicted beam traversal path 304 is divided in smaller segments and defects are assumed to be located along the beam traversal path 304 in each of the segments. The temporal map of predicted time of flight geometric feature response to the incident ultrasound beam is determined based on the assumed defect locations. Further, the received geometric feature response is compared to the predicted geometric feature response. The received geometric feature response, according to certain embodiments, is provided to the processor 106 for comparison with the predicted time of flight geometric feature response through the user interface 108. In other embodiments, the received geometric feature response may be read by the processor 106 from the memory 110 for comparison.

A point in the volumetric representation 402 of the object 102 may be determined to be the location of the geometric feature when the time of flight of the received geometric feature response is equivalent to the predicted time of flight geometric feature response corresponding to the point. For example, in the illustrated example, the item 404 depicts the points where the time of flight of the received geometric feature response is equivalent to the predicted time of flight geometric feature response. Further, a longitudinal section in the predicted beam traversal path 304 for which the predicted time of flight geometric feature response may be equivalent to the received geometric feature response may be determined as the location of the geometric feature. In such a case, the location of the geometric feature may be a band of points in the volumetric representation 402 of the object 102.

Further, in certain embodiments, the locations of the geometric features are displayed with respect to coordinates of the points 404 on X, Y, and Z axes 406. Axes 406 respectively run along the length, width, and height of the volumetric representation 402 of the object 102. For example, from the volumetric representation 402, the location for points 404 is expressed in terms of corresponding points on the X, Y, and Z axes.

In one embodiment, the point 404 is displayed on the volumetric representation 402 on the user interface 108. In certain embodiments, when the operator enters the time of flight of the received geometric feature response through the user interface 108, the processor 106 determines the point 404 for which the corresponding predicted time of flight geometric feature response is equivalent to the received geometric feature response entered by the operator and displays the point 404 on the volumetric representation 402 on the user interface 108. The processor 106 compares the entered time of flight with each point from the temporal map of the predicted time of flight geometric response. Each point in the predicted time of flight geometric response is spatially located on the volumetric representation 402 of the object 102. The point 404 for which the entered time of flight equals the predicted time of flight geometric feature response is determined as the location of the geometric feature. The location of the geometric feature, in certain embodiments, may be displayed on the user interface 108 as a function of the axes 406.

Figure 5:
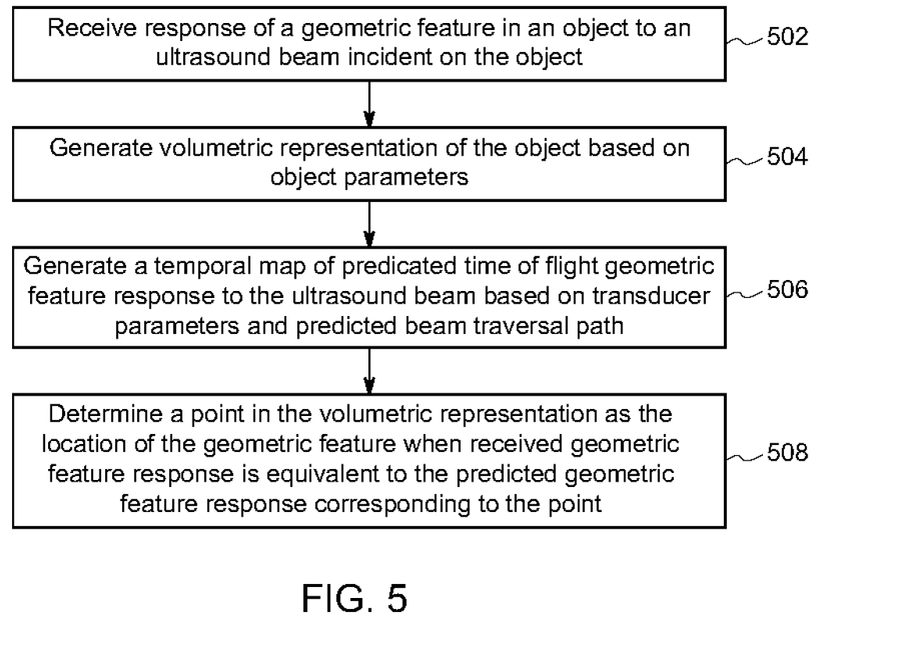
FIG. 5 illustrates a method for locating geometric features in an object, according to one embodiment of the present invention.

FIG. 5 is a flow diagram illustrating a method for determining the location of geometric features in the object 102. To begin, ultrasound beams generated from one of the plurality of transducers 104 are transmitted to be incident on the object 102. At 502, a response of the geometric feature to the incident ultrasound beam is received by one of the transducers 104. At 504, a volumetric representation 402 of the object 102 is generated based on the plurality of object parameters. The object parameters may include object size, thickness, and diameter, for example. At 506, a temporal map of a predicted time of flight geometric feature response is generated. The predicted time of flight geometric feature response is generated based on the predicted ultrasound beam traversal path 302 in the object 102. The predicted ultrasound beam traversal path 302, in turn, is generated based on the volumetric representation 402 and a plurality of transducer parameters. Transducer parameters that influence the predicted beam traversal path 302 from the transducer 104 transmitting the ultrasound beam include, but are not limited to, angle of incidence of the transducer 104, position of the transducer 104 with respect to the object 102, geometry of the transducer 104, and frequency of the transducer 104. At 508, a point 404 on the volumetric representation 402 is determined as the location of the geometric feature when the time of flight of the received geometric feature response is equivalent to the predicted time of flight geometric feature response corresponding to the point 404.

In certain embodiments, to detect presence of the geometric features, the predicted time of flight geometric feature response is calculated by assuming presence of no single defect along the beam traversal path 304. The received geometric feature response is then compared with such a predicted time of flight geometric feature response by the processor 106. When the received geometric feature response is not equivalent to any point from the predicted time of flight geometric feature response, the presence of a geometric feature is detected by the processor 106.

In certain embodiments, the points 404 may be color-coded to indicate at least one of a magnitude of the geometric feature, and accuracy of the determination of the location of the geometric feature response. The magnitude of the geometric feature, for example the size of the anomaly being detected, may be determined based on the amplitude of the geometric feature response for the ultrasound beam.

Further, after the point 404 is determined, the location of the point 404 on the object 102 is stored in the memory 110. The information stored in the memory 110 is utilized to calibrate errors that may occur when determining geometric features in a new object. The processor 106 is configured to compare the location of the point 404 stored in the memory 110 with an actual location of the geometric feature in the object 102. The comparison is utilized to calibrate an error that occurs in the determination of the geometric features in the object 102.

Furthermore, the reference run of inspection carried out before the object 102 is being inspected may be utilized to calibrate the speed of the ultrasound beam in the object 102. During the reference run, when the location of the geometric feature is known, the time of flight information is received for the known geometric feature. The predicted beam traversal path 304 is determined for the reference run and the location of the known geometric feature is determined utilizing the aforementioned technique. If the location of the geometric feature is observed to be different from the known location, the speed of the ultrasound beam may be adjusted such that the determined location matches the known location of the geometric feature.

In certain embodiments, the received geometric feature response and the predicted time of flight geometric response are compared to determine an orientation of the geometric feature in the object 102 being tested. When the received geometric feature response does not correspond to any point in the predicted time of flight geometric feature response, the processor 106 may determine an orientation angle of the geometric feature with respect to the object 102, through the predicted beam traversal path 304. Further, in certain embodiments, it may also be determined whether the geometric feature is oriented at an angle with respect to a normal axis of the object 102 by comparing geometric feature responses received from the geometric feature to multiple ultrasound beams transmitted by the transducer 104 from different positions along the object 102.

Further, in certain embodiments, when the location of a geometric feature in the object 102 is known, the predicted time of flight geometric feature response is compared with the received geometric feature response to determine a configuration of transducers 104 required to cause the transmitted ultrasound beams to be incident on the geometric feature at a required angle. A point of incidence of the ultrasound beam for the ray from the predicted beam traversal path 304 that has a geometric feature response equivalent to the received geometric feature response is determined. The point of incidence is then used to change the configuration of transducers 104 in such a way that the incident ultrasound beam meets the object 102 at the required angle.

Various embodiments described above thus provide for a method and a system for determination of geometric features in the object. The determination of location on the volumetric representation provides for an intuitive representation of the geometric feature in the object. The volumetric display also provides an accurate location of the defect that allows operators to take faster corrective actions. Further, the system and the method reduce the complexity involved in interpreting the currently available response chart from ultrasound inspection systems. Furthermore, limited information available from transducers is utilized to determine the location of geometric features, thus reducing the amount of processing time to determine the locations. In the method, multiple transducers or multiple incident angles of ultrasound beams incident on the geometric features are also utilized to refine determination of location of the geometric features.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of ordinary skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," etc. are used merely as labels, and are not intended to impose numerical or positional requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose several embodiments of the invention, including the best mode, and also to enable any person of ordinary skill in the art to practice the embodiments of invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described method and system for determination of location of geometric features in an object, without departing from the spirit and scope of the invention herein involved, it is intended that all of the subject matter of the above description or shown in the accompanying drawings shall be interpreted merely as examples illustrating the inventive concept herein and shall not be construed as limiting the invention.

What is claimed is:

1. A method to determine a location of at least one geometric feature in an object, the method comprising:
    receiving, by at least a first ultrasound transducer and a second ultrasound transducer from among a plurality of ultrasound transducers, at least two geometric feature responses to at least two ultrasound beams incident on the object and into the same area of interest in the object, wherein the ultrasound beam is produced from an other ultrasound transducer from among the plurality of ultrasound transducers, wherein the first ultrasound transducer and the second ultrasound transducer are arranged at an angle with respect to the object;
    generating, by a processor, a volumetric representation of the object based on a plurality of object parameters;
    generating, by the processor, a temporal map of a predicted time of flight of the received geometric feature responses in response to the ultrasound beams based on a predicted ultrasound beam traversal path in the object that originates from the other ultrasound transducer, wherein the temporal map includes a list of time of flight information of one or more of the ultrasound beams calculated based on the presence of geometric features along a plurality of rays for each of the ultrasonic beams;
    determining, by the processor, a position of the at least one geometric feature on the volumetric representation of the object during generation of the temporal map as the location of the geometric feature, wherein determining comprises:
        receiving, via a user interface, a time of flight of the received geometric feature responses,
        determining, by the processor, a point that corresponds to the predicted time of flight of geometric feature response equivalent to the received geometric feature responses received via the user interface, and
        comparing the locations determined through the geometric feature responses to determine a final location of the geometric feature;
    responsive to the determination, displaying, on the user interface, a point on the volumetric representation;
    analyzing, by the processor, the received time of flight with each point from the temporal map of the predicted time of flight of geometric feature response that determines the location of the at least one geometric feature; and
    displaying, on the user interface, the location of the at least one geometric feature.

2. The method as recited in claim 1, wherein the predicted ultrasound beam traversal path is a representation of a path the ultrasound beam takes inside the object.

3. The method as recited in claim 1, comprising calibrating the plurality of ultrasound transducers with respect to the object prior to collecting the geometric feature responses.

4. The method as recited in claim 1, wherein the at least one geometric feature comprises an anomaly observed in the object.

5. The method as recited in claim 1, further comprising generating, by the processor, a 1-dimensional response chart responsive to the at least one geometric feature response received from the object.

6. The method as recited in claim 5, wherein the 1-dimensional response chart comprises amplitude information for the response received for the ultrasound beam from the at least one geometric feature.

7. The method as recited in claim 1, wherein the plurality of object parameters comprises at least one of diameter of the object, length of the object, geometry of the object, and thickness of the object.

8. The method as recited in claim 1, wherein the plurality of transducer parameters comprises location of the ultrasound transducer along the object, size of the transducer, angle of incidence for the transducer, and frequency of the transducer.

9. A system to determine a location of at least one geometric feature in an object, the system comprises:
    at least two ultrasound transducers arranged at an angle with respect to the object and each configured to transmit an ultrasound beam into the same area of interest of the object and to each receive a geometric feature response to the ultrasound beam; and
    a processor configured to:
    generate a volumetric representation of the object based on a plurality of object parameters;
    generate a temporal map of predicted time of flight of the received geometric feature responses in response to the ultrasound beam based on predicted ultrasound beam traversal paths in the object that originate from the two ultrasound transducers,
        wherein the temporal map includes a list of time of flight information of one or more of the ultrasound beams calculated based on the presence of geometric features along a plurality of rays for each of the ultrasonic beams;
    determine a position of the geometric feature on the volumetric representation of the object during generation of the temporal map as the location of the geometric feature, when the received geometric feature responses are equivalent to the predicted time of flight of the geometric feature response corresponding to the position, wherein the determination comprises receiving, via a user interface, an entered time of flight of the received geometric feature response, wherein the processor determines the point that corresponds to the predicted time of flight geometric feature response equivalent to the received geometric feature responses received via the user interface and compares the locations determined through the two geometric feature responses to determine a final location of the geometric feature;
    responsive to the determination, display, on the user interface, a point on the volumetric representation;
    analyze the received time of flight with each point from the temporal map of the predicted time of flight geometric feature response that determines the location of the geometric feature; and
    display, on the user interface, the location of the geometric.

10. The system as recited in claim 9, wherein the predicted ultrasound beam traversal path is a representation of a path the ultrasound beam takes inside the object from the ultrasound transducer.

11. The system as recited in claim 9, wherein the at least one geometric feature response to the ultrasound beam is represented in the form of a 1-dimensional response chart.

12. The system as recited in claim 11, wherein the 1-dimensional response chart comprises amplitude information for the at least one geometric feature response received from the geometric feature.

13. The system as recited in claim 9, wherein the plurality of object parameters comprises at least one of diameter of the object, length of the object, geometry of the object, and thickness of the object.

14. The system as recited in claim 9, wherein the plurality of transducer parameters comprises at least one of location of the ultrasound transducer along the object, angle of incidence for the transducer, size of the transducer, and frequency of the transducer.

15. The system as recited in claim 9 further comprises a data repository to store locations of the geometric features in the object.

16. The system as recited in claim 15, wherein the processor is further configured to calibrate an error in the locations of geometric features in a new object based on a comparison between actual locations of the geometric features in the object with data stored in the data repository.

17. A non-transitory computer readable media embodying computer executable instructions, which when executed by a processor cause the computer to perform a method to determine a location of at least one geometric feature in an object, comprising computer-executable instructions to:
  receive, by at least two ultrasound transducers from among a plurality of ultrasound transducers, geometric feature responses in response to ultrasound beams incident on the object and produced by at least one ultrasound transducer, wherein the at least two transducers are arranged at an angle with respect to the object and each of the at least two transducers are configured to transmit an ultrasound beam into the same area of interest;
  generate, by the processor, a volumetric representation of the object based on a plurality of object parameters;
  generate, by the processor, a temporal map of predicted time of flight of the received geometric feature responses to the ultrasound beam based on a predicted ultrasound beam traversal path in the object that originates from the ultrasound transducer,
    wherein the temporal map includes a list of time of flight information of one or more of the ultrasound beams calculated based on the presence of geometric features along a plurality of rays for each of the ultrasonic beams;
  determine, by the processor, a position of the geometric feature on the volumetric representation of the object as the location of the geometric feature during generation of the temporal map, when the received geometric feature responses are equivalent to the predicted time of flight of the geometric feature response corresponding to the position, wherein the determination comprises receiving, via a user interface, the time of flight of the received geometric feature responses, wherein the processor determines the point that corresponds to the predicted time of flight geometric feature response equivalent to the received geometric feature responses received from the user interface, and wherein the processor compares the locations determined through the geometric feature responses to determine a final location of the geometric feature;
  responsive to the determination, display, on the user interface, a point on the volumetric representation;
  analyze the received time of flight with each point from the temporal map of the predicted time of flight geometric feature response that determines the location of the geometric feature; and
  display, on the user interface, the location of the geometric feature.

* * * * *